United States Patent
Rübsamen et al.

(10) Patent No.: US 10,837,007 B2
(45) Date of Patent: Nov. 17, 2020

(54) RECOMBINANT FUSION PROTEINS FOR PREVENTING OR TREATING ADHESIONS OF TISSUES OR ORGANS

(71) Applicant: Akesion GmbH, Schriesheim (DE)

(72) Inventors: Klaus Rübsamen, Neustadt (DE); Stephan Witte, Schriesheim (DE)

(73) Assignee: Akesion GmbH, Schriesheim (DE)

( * ) Notice: Subject to any disclaimer, the term of this patent is extended or adjusted under 35 U.S.C. 154(b) by 0 days.

(21) Appl. No.: 15/506,558

(22) PCT Filed: Aug. 20, 2015

(86) PCT No.: PCT/EP2015/069176
§ 371 (c)(1),
(2) Date: Feb. 24, 2017

(87) PCT Pub. No.: WO2016/030278
PCT Pub. Date: Mar. 3, 2016

(65) Prior Publication Data
US 2017/0253864 A1    Sep. 7, 2017

(30) Foreign Application Priority Data
Aug. 26, 2014  (DE) .................. 10 2014 112 212

(51) Int. Cl.
| C12N 9/64 | (2006.01) |
| A61K 38/48 | (2006.01) |
| C07K 19/00 | (2006.01) |
| C07K 16/46 | (2006.01) |
| A61L 31/04 | (2006.01) |
| C07K 14/765 | (2006.01) |
| A61K 38/00 | (2006.01) |

(52) U.S. Cl.
CPC .......... *C12N 9/6424* (2013.01); *A61K 38/482* (2013.01); *A61L 31/047* (2013.01); *C07K 14/765* (2013.01); *C12Y 304/21074* (2013.01); *A61K 38/00* (2013.01); *C07K 2319/30* (2013.01); *C07K 2319/31* (2013.01)

(58) Field of Classification Search
None
See application file for complete search history.

(56) References Cited

U.S. PATENT DOCUMENTS

| 5,578,305 | A | 11/1996 | Franz et al. | |
| 6,214,594 | B1 | 4/2001 | Markland et al. | |
| 6,461,640 | B1* | 10/2002 | Hubbell | A61K 38/58 424/484 |
| 6,818,018 | B1* | 11/2004 | Sawhney | A61L 27/34 523/113 |
| 8,158,610 | B2* | 4/2012 | Brown | A61K 31/198 514/58 |
| 8,629,314 | B2 | 1/2014 | Van Holten et al. | |
| 2004/0224006 | A1 | 11/2004 | Raffaniello | |
| 2005/0074865 | A1* | 4/2005 | Afeyan | C12N 9/00 435/226 |
| 2008/0254091 | A1 | 10/2008 | Lee et al. | |
| 2008/0274096 | A1* | 11/2008 | Andersson | C12N 9/6489 424/94.63 |
| 2009/0175893 | A1 | 7/2009 | Mertins et al. | |
| 2013/0165389 | A1 | 6/2013 | Schellenberger et al. | |
| 2014/0017273 | A1 | 1/2014 | Sleep et al. | |
| 2014/0178375 | A1* | 6/2014 | Greene | C07K 16/32 424/134.1 |

FOREIGN PATENT DOCUMENTS

| EP | 0227400 A2 | 7/1987 | | |
| EP | 0297860 A1 | 1/1989 | | |
| EP | 0318801 A2 | 6/1989 | | |
| EP | 0395375 A1 | 10/1990 | | |
| EP | 0517756 B1 | 11/1994 | | |
| EP | 0473689 B1 | 12/1994 | | |
| EP | 0874634 B1 | 3/2002 | | |
| EP | 3185891 B1 * | 4/2020 | | A61K 38/48 |
| WO | 9515747 A1 | 6/1995 | | |
| WO | 9929838 A1 | 6/1999 | | |
| WO | WO-2007090584 A1 * | 8/2007 | | C07K 14/76 |

OTHER PUBLICATIONS

Yang et al., Cloning and expression of defibrase cDNA from the venom of Gloydius Sheadaoensis, Biotechnol. Lett., 2002, 24, 135-38.*
Ishii et al., The nucleotide sequence of the cloned nusA gene and its flanking region of *Escherichia coli*, Nucleic Acid Res., 1984, 12, 3333-42.*
Jiang et al., Molecular mechanism analysis of Gloydius sheadaoensis venom gloshedobin ineraction with inhibitors by homology modeling, Int. J. Biological Marcomolecules, 2011, 48, 129-33.*
You et al., Functional characterization of recombinant batroxobin, a snake venom thrombin-like enzyme, expressed from Pichia pastoris, FEBS Lett., 2004, 571, 67-73.*
Linderholm et al., Immunoglobulin Fc-fusion proteins, BioProcess International, 2014, 12, 20-27.*

(Continued)

*Primary Examiner* — Robert B Mondesi
*Assistant Examiner* — Todd M Epstein
(74) *Attorney, Agent, or Firm* — Insigne LLP

(57) ABSTRACT

The invention relates to recombinant fusion proteins comprising a fibrinogenolytic enzyme having an amino acid sequence that is C-terminally and/or N-terminally linked to the amino acid sequence of at least one high-molecular inert stabilization domain with a molecular weight of >50 kDa, for the prevention or treatment of adhesions at tissues or organs, in particular peritoneal adhesions following surgical interventions.

8 Claims, 2 Drawing Sheets
Specification includes a Sequence Listing.

(56) References Cited

OTHER PUBLICATIONS

Xiuping Jiang, et al. "Soluble Expression, Purification, and Characterization of Gloydius Shedaoensis Venom Gloshedobin in *Escherichia coli* by Using Fusion Partners", Biotechnologyically Revelant Enzymes and Proteins, Jul. 2009, vol. 85 pp. 635-642.
English translation of International Search Report & Written Opinion of the International Searching Authority issued in International Application No. PCT/EP2015/069176 dated Oct. 14, 2015.
Bart W. J. Hellebrekers et al., "A role for the fibrinolytic system in postsurgical adhesion formation", Jan. 2005, pp. 122-129, vol. 83, No. 1, Elsevier Inc.
Bart W. J. Hellebrekers et al., "Pathogenesis of postoperative adhesion formation", British Journal of Surgery, 2011, pp. 1503-1516, vol. 98, John Wiley & Sons Ltd.
Willy Arung et al., "Pathophysiology and prevention of postoperative peritoneal adhesions", World Journal of Gastroenterology, Nov. 7, 2011, pp. 4545-4553, vol. 17, Issue 41, Baishideng.
Harold Ellis et al., "Adhesion-related hospital readmissions after abdominal and pelvic surgery: a retrospective cohort study", The Lancet, May 1, 1999, pp. 1476-1480, vol. 351.
Michael C. Parker et al., "Postoperative Adhesions: Ten-Year Follow-Up of 12,584 Patients Undergoing Lower Abdominal Surgery", Diseases of the Colon & Rectum, 2001, pp. 822-829, vol. 44, No. 6.
Michael C. Parker et al., "The SCAR-3 study: 5-year adhesion-related readmission risk following lower abdominal surgical procedures", Colorectal Disease, 2005, pp. 551-558, vol. 7, Blackwell Publishing Ltd.
Richard P. G. ten Broek et al., "Burden of adhesions in abdominal and pelvic surgery: systematic review and met-analysis", British Medical Journal, Oct. 3, 2013, pp. 1-15, vol. 347.
Tea H.I. Brummer et al., "FINHYST, a prospective study of 5279 hysterectomies: complications and their risk factors", Human Reproduction, 2011, pp. 1741-1751, vol. 26, No. 7, Oxford University Press.
J. Kössi et al., "Population-based study of the surgical workload and economic impact of bowel obstruction caused by postoperative adhesions", British Journal of Surgery, 2003, pp. 1441-1444, vol. 90, John Wiley & Sons Ltd.
Vanja Sikirica et al., "The inpatient burden of abdominal and gynecological adhesiolysis in the US", BMC Surgery, 2011, pp. 1-9, vol. 11, No. 13, BioMed Central Ltd.
Nancy Fox Ray et al., "Abdominal Adhesiolysis: Inpatient Care and Expenditures in the United States in 1994", Journal of American College of Surgeons, Jan. 1998, pp. 1-9, vol. 186, No. 1, Elsevier Science Inc.
Beat Schnüriger et al., "Prevention of postoperative peritoneal adhesions: a review of the literature", The American Journal of Surgery, 2011, pp. 111-121, vol. 201, Elsevier Inc.
Richard P. G. ten Broek et al., "Different surgical techniques to reduce post-operative adhesion formation: a systematic review and meta-analysis", Human Reproduction Update, 2013, pp. 12-25, vol. 19, No. 1, Oxford University Press.
Markus Wallwiener et al., "A European survey on awareness of post-surgical adhesions among gynaecological surgeons", Gynecological Surgery, 2014, pp. 105-112, vol. 11, Springer.
Gregory T. Fossum et al., "Gynecologic use of Sepraspray Adhesion Barrier for reduction of adhesion development after laparoscopic myomectomy: a pilot study", Fertility and Sterility, Aug. 2011, pp. 487-491, vol. 96, No. 2, Elsevier Inc.

Ghassan M. Saed et al., "Molecular Characterization of Postoperative Adhesions: The Adhesion Phenotype", The Journal of the American Association of Gynecologic Laparoscopists, Aug. 2004, pp. 307-314, vol. 11, No. 3, The American Association of Gynecologic Laparoscopists.
Marcel Binnebösel et al., "Chronological evaluation of inflammatory mediators during peritoneal adhesion formation using a rat model", Langenbeck's Archives of Surgery, 2011, pp. 371-378, vol. 396, Springer-Verlag.
Michael P. Diamond et al., "Effect of Tisseel® on expression of tissue plasminogen activator and plasminogen activator inhibitor-1", Fertility and Sterility, Jun. 2004, pp. 1657-1664, vol. 81, No. 6, Elsevier Inc.
Maria Mercedes Binda et al., "Effect of Reteplase™ and PAI-1 antibodies on postoperative adhesion formation in a laparoscopic mouse model", Surgical Endoscopy, 2009, pp. 1018-1025, vol. 23, Elsevier Inc.
Jennifer L Hill-West et al., "Local Release of Fibrinolytic Agents for Adhesion Prevention", Journal of Surgical Research, 1995, pp. 759-763, vol. 59, Academic Press, Inc.
Bart W. J. Hellebrekers et al., "Preoperative predictors of postsurgical adhesion formation and the Prevention of Adhesions with Plasminogen Activator (PAPA-study): results of a clinical pilot study", Fertility and Sterility, Apr. 2009, pp. 1204-1214, vol. 91, No. 4, Elsevier Inc.
E.C. Ashby et al., "The Effect of Intraperitoneal Malayan Pit-viper Venom on Adhesion Formation and Peritoneal Healing", British Journal of Surgery, Nov. 1970, pp. 863, vol. 57, No. 11.
Robert F. Buckman, Jr., et al, "Prevention of Experimental Postoperative Adhesions by Ancrod Defibrinogenation", Journal of Surgical Research, 1975, pp. 377-384, vol. 18, Academic Press, Inc.
Sanghamitra M. Chowdhury et al., "Adhesion Prevention with Ancrod Released via a Tissue-Adherent Hydrogel", Journal of Surgical Research, 1996, pp. 58-64, vol. 61, Article No. 0081, Academic Press, Inc.
Martin Schlapschy et al., "PASylation: a biological alternative to PEGylation for extending the plasma half-life of the plasma half-life of pharmaceutically active proteins", Protein Engineering, Design & Selection, 2013, pp. 489-501, vol. 26, No. 8, Oxford University Press.
W. J. A. Brokelman et al., "Peritoneal changes due to laparoscopic surgery", Surgical Endoscopy, 2011, pp. 1-9, vol. 25, Springer.
Zane Cohen et al., "Prevention of Postoperative Abdominal Adhesions by a Novel, Glycerol/Sodium Hyaluronate/Carboxymethylcellulose-Based Bioresorbable Membrane: A Prospective, Randomized, Evaluator-Blinded Multicenter Study", Diseases of the Colon & Rectum, 2005, pp. 1130-1139, vol. 48, The American Society of Colon and Rectal Surgeons.
Paul J. Klingler et al., "Seprafilm® -Induced Peritoneal Inflammation: A Previously Unknown Complication" Diseases of the Colon & Rectum, Dec. 1999, pp. 1639-1642, vol. 42, No. 12, Springer.
Author Unknown, "Pathogenesis, consequences, and control of peritoneal adhesions in gynecologic surgery: a committee opinion", Fertility and Sterility, Mar. 4, 2013, pp. 1-7, Practice Committee of the American Society for Reproductive Medicine in collaboration with the Society of Reproductive Surgeons, Birmingham, Alabama.
Daping Yang et al., "Expression, purification and characterization of Gloydius shedaoensis venom gloshedobin as Hsp70 fusion protein in Pichia pastoris", Protein Expression and Purification, 2009, pp. 138-142, vol. 66, Elsevier Inc.

* cited by examiner

RECOMBINANT FUSION PROTEINS FOR PREVENTING OR TREATING ADHESIONS OF TISSUES OR ORGANS

DESCRIPTION

Under normal healing conditions the mammalian organism responds to injury with specifically running wound healing processes. These result in the production of fibrin, a sticky substance, responsible for wound healing. Fibrinogen, the precursor of fibrin, circulates in the blood and occurs in the area of injury as wound fluid (exsudate). Due to the action of the locally formed thrombin, fibrinogen is converted to insoluble fibrin, so that the wound is sealed within a few minutes. Excess fibrin is removed rapidly by the simultaneously activated endogenous fibrinolytic system mediated by the action of plasmin.

TECHNICAL FIELD

Tissue agglutinations or adhesions are the result of misdirected wound healing processes, which is attributed to an imbalance of the endogenous fibrinolytic system (Hellebrekers et al, 2005; Hellebrekers & Kooistra, 2011). In accident- or surgery-related injuries in the abdominal area, the removal of fibrin is impaired by the activation of inhibitors of plasmin, in particular by PAI-1, PAI-2 and $a_2$-antiplasmin. Excess fibrin that has not been removed results in an agglutination of adjacent tissues and organs, which are converted within a few days by the growth of fibroblasts and blood vessels into permanent adhesions (Arung et al., 2011). These adhesions can occur both between different organs and also between organs and the peritoneum. The resulting limited mobility of the organs is noticeable in many cases by chronic pain or, in female patients, by infertility and can, in severe cases, result in a life-threatening intestinal blockage caused by the impairment of peristalsis.

STATE OF THE ART

A retrospective analysis of the Scottish National Health Service Medical Record Linkage Database revealed that in more than half of all surgical procedures there are adhesions in the abdominal area (Ellis et al. 1999). In approximately one third of the patients with adhesions the clinical symptoms were so severe that they had to be re-operated in the first year after surgery. The high number of multiple operations shows that the risk of further adhesions increases significantly with the number of operations (Parker et al, 2001, 2005).

A meta-analysis of 196 studies with a total of 1,50,797 patients showed that up to 9% of abdominal surgery, an intestinal obstruction occurred as a serious complication (Broek et al., 2013a), wherein the adhesions were confirmed intra-operatively in emergency surgery in 2% of intestinal obstruction. In 6% of post-operations that were carried out to remove adhesions, serious consequential damages were caused to internal organs. Injuries to the intestine during surgical removal of adhesions represented the most important isolated risk factor (Brummer et al. 2011). The additional costs of time and material caused by the adhesions are considerable. With 138 hospitalisations for postoperative intestinal obstructions (Kossi et al. 2003) a total of 1118 inpatient days were required.

On the basis of data of "2005 Healthcare Cost and Utilization Project's Nationwide Inpatient Sample", Sikirica et al. (2011) calculated a total cost of $ 2.3 billion to remedy the adhesion-caused operational consequences. Of this amount, 1.4 billion USD accounted for primary adhesiolysis and 926 million USD for secondary adhesiolysis. The adhesion-caused cases of abdominal operations caused a total of 57,005 extra days in hospital. An analysis of sickness data on the basis of the US "National Hospital Discharge Database", 1994, showed that for subsequent removal of adhesions a total 846,415 additional hospital days were required, resulting in an additional cost of 1.3 billion USD annually (Ray et al., 1998).

These pharmaco-economic data support the need for and the potential benefits of an effective and safe adhesion prevention both for the individual patients and for the health care system. The only possible therapy of peritoneal adhesions is surgical separation of conjoined surfaces and organs. Due to the increased risk for the development of further adhesions by the renewed intervention, prophylactic methods that are likely to reduce the risk of the formation of adhesions, become particularly important.

As prophylactic methods for preventing agglutinations or adhesions, either the surgical technique can be optimized or mechanical methods for physical separation of the injured surfaces can be utilized. Finally, there are pharmacological approaches for influencing the underlying patho-physiological processes (summarized in Arung et al, (2011); Schnuriger et al, (2011)).

Due to the use of minimal invasive surgical techniques (laparoscopy), the risk of agglutinations and adhesions appears to be slightly lower in comparison to the conventional surgical technique with open abdomen (laparotomy) (Broek et al, 2013b; Schnuriger et al, 2011). The difference is probably due to the smaller wound surface in comparison to laparotomy, less manipulation of tissues and organs, as well as the generally lower risk of infection of this surgical technique (SCAR Group, 2013). Despite numerous improvements in surgical technique, the adhesions, as a result of surgical procedures in the abdominal area, still represent an unchanged high risk of complications, such as chronic pain, infertility or even intestinal obstruction (Wallwiener et al., 2014).

Another method currently used to reduce the risk of postoperative adhesions is the mechanical separation of the wounded tissue areas by the use of barriers of different biocompatible materials or by the instillation of a larger amount of fluid in the abdominal cavity. The most commonly used measure is the introduction of thin membranes of biodegradable materials, which are introduced between the wounded areas and fixed there. Due to the mechanical separation of organ surfaces, these can heal in an isolated way, which should lead to the prevention of adhesions. Compositions such as hyaluronic acid and carboxy-methylcellulose (Seprafilm) are placed, for example, as a membrane on the injured surface. Further, hyaluronic acid has been used to prevent adhesions in a myomectomy, resulting in a reduction of agglutinations (Fossum et al. 2011). Other known compositions are gel-forming polyethylene glycols, polyethylene oxide in combination with sodium carboxymethylcellulose or oxygenated regenerated cellulose. Further examples of such adhesion barriers are described in the published patent application U.S. Pat. No. 8,629,314 A, and in the form of a novel multilayer adhesion barrier in US 20080254091 A.

Some experimental approaches deal with the use of chemical substances with the aim of intervening in the patho-physiological process of adhesion formation at an early stage. This initial phase of adhesio, which only last a few hours is characterized by a persistent local inflammation and clot activation, followed by increased vascular permeability, resulting in an accumulation of a fibrin-rich exudate covering the surface (Hellebrekers and Kooistra 2011). Conditions such as tissue hypoxia (Saeed and Diamond 2004) and the cytokines-induced cellular immune reaction which is caused by macrophages and T cells are augmented factors for the formation of adhesions (Binnebosel et al. 2011). Already on the second day, the wound surface is covered by macrophages, fibroblasts and mesothelial cells, which come together in a short time to form a closed layer, penetrated by mast cells, fibroblasts and newly formed endothelial cells. This irreversible formation of a solid matrix is the basis for further coalescence, characterized by band-like collagen fibrils and growing-in of blood vessels and connective tissue fibres.

The central event in the formation of adhesions is thus the formation of a local fibrin from the precursor fibrinogen. Under normal conditions there is a balance between fibrin formation and fibrin reduction by plasmin, whose enzymatic activity is in turn controlled by the inhibitors PAI-1, PAI-2 and $\alpha_2$-antiplasmin. Experimental data show that fibroblasts that occur in the area of adhesions, have a reduced concentration of plasminogen activator at elevated plasminogen activator-inhibitor formation, which supports the uncontrolled formation of a fibrin matrix (Diamond et al. 2004). This observation was confirmed in a prospective study of patients with endometriosis (Hellebrekers et al. 2005).

The inhibition of inflammatory reaction, the increase in fibrinolytic activity and the impact of the clotting thus seemed to be the useful therapeutic targets, in order to prevent the formation of adhesions. In numerous experiments, attempts were made to compensate for the lack of endogenous fibrinolytic activity by administering fibrinolytic active substances. EP 0318801B1, U.S. Pat. No. 5,578,305A, EP 029786061 and EP 022740061 describe, for example, the use of rt-PA in hydroxyethyl cellulose hydrogel and other matrices to be effective in preventing adhesions. Even r-tPA modifications with increased fibrin affinity have been proposed for this application (EP 0517756B1). The inhibition of fibrin formation, as described in EP 087463461, by using thrombin inhibitors, represents another approach to prevent the adhesion at an early stage. EP 047368961 describes the use of plasminogen activators, such as urokinase, streptokinase and t-PA and refers to the short half-life period in blood. As a solution, the coupling of plasminogen activators to a fibrin fragment is suggested.

Due to repeated intraperitoneal administration of rt-PA, the formation of adhesions was reduced in a mouse model, wherein the effect was, however, not dose-dependent (Binda et al. 2009). In an adhesion model in rats, the plasminogen activator t-PA, urokinase or streptokinase was administered over 4 days using either a biodegradable hydrogel matrix or by 4× daily injections. The t-PA released from a matrix reduced the adhesion of 72±15% (control) to 4±3%, while intraperitoneal injections reduced adhesions only to 49±8% (Hill-West et al. 1995). In summary, the results obtained with fibrinolytic substances are unsatisfactory.

Despite these negative experimental findings, rt-PA was tested in a prospective study of 26 patients with myomectomy under clinical conditions (Hellebrekers et al. 2009). A significant difference in the frequency of adhesions between the two groups could not be observed. The frequency and severity of adhesions were correlated with the PAI-1 concentrations measured before surgery and therefore refer to the importance of the fibrinolytic system for adhesion formation. However, for successful prevention, relatively high t-PA concentrations are required that have not been achieved in this study because of the short biological half-life of rt-PA. Thus, these substances are not suitable for a preventive or therapeutic use to prevent adhesions in tissue compartments after injuries of the abdominal area.

All previously used pharmacological methods for reducing the risk of adhesions generally proved to be rather ineffective in clinical trials.

In particular, the efficacy of fibrinolytic active substances was disappointing. This is presumably due to the fact that the fibrinolytic activity of exogenously administered fibrinolytic substances is inhibited by high concentrations of plasminogen-activator inhibitor (PAI-1, PAI-2) occurring during bonding. In order to achieve a sufficient efficacy of fibrinolytic substances, very high dosages are required, but due to the absorption of these substances through the peritoneal membrane they result in systemic side effects, particularly bleedings. The prevention that is free from side effects or early resolution of the resulting fibrin bridges as cause of adhesions is thus not guaranteed.

The removal of fibrinogen, the precursor of fibrin, seems thus more promising in order to inhibit its formation at an early stage. The suitability of fibrinogenolytic enzymes for the prevention of postoperative adhesions was experimentally studied on animals using isolated enzyme ancrod of the venom of the Malayan pit viper, Calloselasma rhodostoma (Ashby et al, 1969;. Buckman et al, 1975; Chowdhury, & Hubbell, 1996). Ancrod specifically cuts the arginine-glycine bonding of A$\alpha$-chain of fibrinogen. Unlike thrombin, the B$\beta$-chain is not cut by ancrod. The resulting des-A-fibrin monomers polymerize after the splitting of fibrinopeptides to short chain soluble fibrin, which is not cross-linked and is rapidly eliminated by the reticuloendothelial system and plasmin. By intravenous or intraperitoneal administration of ancrod the fibrinogen concentration in the blood can be reduced in a controlled manner. In the studies as cited, this resulted in a near complete, dose-dependent inhibition of adhesion formation. Because of the low molecular weight of <40 kDa, ancrod can quickly escape from the abdominal area into the blood circulatory system, where it causes inhibition of clotting. In accordance with high blood concentration, this can result in local bleeding.

In addition, pharmaceutical compositions of a fusion protein of ancrod are known, which are used for resolving blood coagulation. For instance, EP 0395375 A1 describes a fusion protein between ancrod and a 5'-terminal polypeptide, which may include 2 to 1000 amino acids. The use of this fusion protein for the treatment of post-operative adhesions, however, is not described therein.

In a similar way acts batroxobin obtained from the venom of the South American snake Bothrops atrox, which likewise selectively splits fibrinogen, thereby reducing the concentration of fibrinogen. A fusion protein between batroxobin and a second polypeptide chain is described, for example, in WO 99/29838 A1.

For many years, ancrod was used, inter alia, to prevent thrombosis in patients with heparin-induced thrombocytopenia and for the treatment of peripheral arterial circulatory disturbances; however, it has since been replaced by newer drugs. However, these and similar enzymes are not suitable for the prophylaxis of peritoneal adhesions despite their good efficacy in animal models, because they do not remain sufficiently long in the abdominal area due to their molecular structure and because they quickly get into the bloodstream and thereby inhibit clotting. This side effect is prohibitive for the indication "Prophylaxis of postoperative adhesions", so that a native application of these substances is not considered for patients.

Further, there are other fibrinogenolytic fusion proteins which, however, have not been developed with the approach to a treatment of peritoneal adhesions. Such constructs are disclosed in U.S. Pat. No. 6,214,594 B1 or in Yang et al, Protein Expression and Purification, 66 (2009). 138-147.

In order to achieve a slow release of the active ingredients and a longer duration of action in peritoneal cavity, fibrinolytic and defibrinogenating substances were, for example, embedded in a carrier material (US 2004/224006 A1). The U.S. Pat. No. 8,629,314 B2 describes the implementation of different active substances into a polymer matrix for the prevention of adhesions. Similar experiments are also disclosed in U.S. Pat. No. 6,461, 640 B1 and WO 1995/15747 A1. Here, a topically applied biodegradable polymer matrix is used as a carrier for plasminogen, urokinase and streptokinase, and ancrod. The success of these measures was low, probably mainly due to the uncontrolled release of the embedded active agents.

SUMMARY OF THE INVENTION

Figure 1:
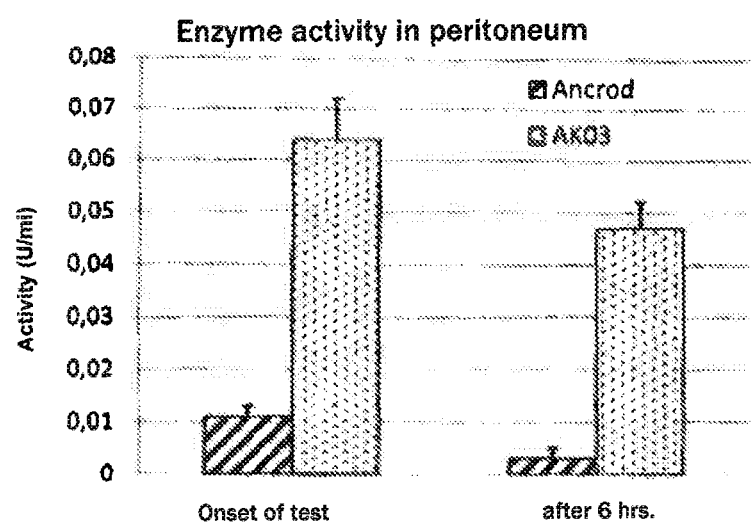
FIG. 1 shows the enzyme activity in the fluid in the abdominal area after a single intra-peritoneal administration of native ancrod and ancrod fusion protein of the invention (AK03).

Against this background, it is the object of the present invention to reduce and prevent the local or systemic side effects associated with the known fibrinolytic or fibrinogenolytic substances, particularly in the form of bleeding or an inhibition of blood clotting, and to provide a pharmacologically active agent, which allows the prevention or reduction of post-operative adhesions. This object is solved by a recombinant fusion protein having the features of claim 1. Preferred embodiments can be found in the dependent claims.

The inventors have surprisingly found out that the undesirable properties of known fibrinogenolytic enzymes for the prophylaxis of post-operative adhesions, particularly in the peritoneal cavity, can be reduced or prevented by linkage to an inert stabilizing domain of high molecular weight. The inventive recombinant fusion proteins enable a preventive treatment of adhesions in tissues or organs, in particular peritoneal adhesions following surgery or injury. In the case of fusion protein, a fibrinogenolytic enzyme or enzyme fragment is linked to an inert stabilization domain of high molecular weight as biologically active domain, whereby a fusion protein arises, which represents a high molecular fibrinogenase with novel enzymatic and pharmacokinetic properties. By linking the fibrinogenolytic enzyme to the inert high molecular weight stabilization domain, the molecular weight is significantly increased and a non-specific bonding to mesothelium surface lining the peritoneal cavity is obtained. Surprisingly, the transport through the peritoneal membrane is reduced and also the transfer into the bloodstream. In addition, the residence time and thus action time of fibrinogenase is extended as recombinant active ingredient in the abdominal area, whereby the chance of successfully treating affected patients (e.g. human or animal) upon application is increased. Due to the longer residence time and action time, the necessary biologically active doses for fibrinogen removal can be drastically reduced, whereby the drawbacks, initially described for fibrinolytic or fibrinogenolytic active substances with reference to symptoms such as bleeding or preventing blood clotting, can be almost completely eliminated or at least significantly reduced.

Preferably, the inert stabilizing domain of high molecular weight relates to a protein α, polypeptide α or a peptide having a molecular weight of more than 50 kDa, preferably a molecular weight of more than 80 kDa. Preferred molecular weights of the stabilization domain, provided for linking to the enzyme domain, lie between 50 and 150 kDa, preferably between 50 and 100 kDa. The desired increased molecular weight of the stabilization domain can also be produced by dimerization or multimerization of the stabilization domain, for example, by dimerization of an IgG-Fc fragment of the human IgG1-Fc fragment. The coupling of the inert stabilization domain of high molecular weight to the fibrinogenolytic enzyme occurs either C-terminal and/or N-terminal. For maintaining the enzymatic activity, the structure of the enzyme domain must be considered here. Optionally, sufficiently long linker sequences must be inserted between the proteins. If a free N- or C-terminus is required for the enzymatic activity, the enzymatic activity in only one of the possible variants is maintained. This can be determined by the expert without undue burden according to known methods, for example, based on activity assays. In a preferred variant, a plurality of stabilization domains can be linked to the C-terminus or N-terminus of the enzyme domain in order to achieve this increase of molecular weight. Also a combination of different stabilization domains (for example, prepared as recombinant expression products) is possible. By linking the stabilization domain to the fibrinogenolytic enzyme, the fibrinogenolytic properties of the enzyme are preserved even in the fusion product, so that the resultant novel recombinant fusion protein is pharmacologically active while simultaneously avoiding the disadvantages mentioned.

A coupling of ancrod to the N-terminus of the stabilization domain has been found to be particularly effective. In particular, an extended residence time of the construct could be detected in the peritoneal cavity as compared to the native ancrod molecule.

The biologically active domain of the recombinant fusion protein causes the enzymatic removal of fibrinogen, thereby preventing the formation of fibrin, the precursor of adhesions. By coupling the enzyme to a stabilization domain based on proteins or peptides, a discharge of the biologically active enzyme components from the abdominal area in the blood circulatory system is reduced or prevented, whereby the effect on the local, excessive fibrin formation is limited and an undesirable prevention of blood coagulation is reduced or prevented. In doing so, bleeding can be prevented without compromising the healing of the surgical wound. Thanks to the increased residence time of the said construct, the residence time of the active substance is further increased so that the formation of adhesions is suppressed via the critical healing phase of 2 to 4 days. For these reasons, the recombinant fusion proteins of the invention are excellent candidates for therapeutic use because they cause little or no side effects compared to the substances tested to date, which is due to the low systemic availability. Further, the substances of the invention have a significantly better efficacy due to the long action duration, so that they are generally suitable for all therapeutic applications that require a long action duration of the active substances.

In a preferred embodiment, the domain encoding the fibrinogenolytic enzyme and the stabilization domain must be interlinked directly via their C-terminus or N-terminus. The coupling of the stabilization domain to the amino acid sequence of the fibrinogenolytic enzyme can be carried out, for example, by methods such as those described in US 2009/0175893A and US 2014/0017273A.

The biological activity of the recombinant fusion protein produced by linking a fibrinogenolytic enzyme to a stabilization domain can be optimized, however, by an additional linker which is arranged between the stabilization domain and enzyme domain. In a preferred embodiment, the inert stabilization domain is therefore connected via a variable linker to the fibrinogenolytic enzyme. The coupling of the linker takes place either via the C-terminus or the N-terminus of the stabilization domains or the enzymatically active domain. For attaching the linker, standard methods as known in prior art can be used.

The linker preferably relates to a peptide or polypeptide, whose amino acid sequence may have a different length or degree of branching. A preferred linker comprises, for example, repetitive sequences of glycine, alanine and serine residues. Preferably, the linker comprises a sequence (GGGGGS)x or (GGGGA)xR, where A=alanine; G=glycine; S=serine; R=arginine; x=number of repeats >1. The number of repetitions x in the linker sequence is preferably between 1 and 4. The linker increases the spherical distance between the fibrinogenolytic enzyme and the inert stabilization domain of the recombinant fusion protein according to the invention.

In addition to the peptide linkers as mentioned above, well-known chemical linkers according to the present invention can be used for linking both domains, whereby their structure and length can be modified within the usual methodology for the orientation of both domains to gain an optimized expression and enzymatic activity of the fusion protein. The constructs of the invention are verified for their biological activity in one of the known assays after their production, in which the fibrinogenolytic enzyme activity of the fusion proteins is determined. More particularly, the invention comprises fusion proteins that are sufficiently fibrinogenolytically active. In order to optimize the biological activity, it may be necessary to adjust the type and position of the coupling, the structure and length of the linker as well as the type and the structure of the stabilizing domain. In particular, a steric obstruction of the stabilization domain affects the enzyme activity adversely, but this can be easily determined by a person skilled in the art using the available means in vitro.

The recombinant fusion proteins of high molecular weight of the present invention thus represent highly effective fibrinogenases, which can be cloned using standard methods and can be expressed in suitable expression systems. Because of the relatively high molecular weight of the constructs and their complex structure, which comprise disulfide bridges, eukaryotic expression systems are preferred.

As used herein, the term "fibrinogenolytic enzyme" comprises enzymes, active enzyme fragments or enzymatically active substances, which have a fibrinogenase activity and cause or promote the degradation of fibrinogen. Preferably, the fibrinolytic enzyme of the fibrinogenase domain relates to a serine protease, preferably a thrombin-like serine protease. Preferred fibrinogenolytic enzymes are, for example, the enzymes ancrod or batroxobin, isolated from snake venoms. These enzymes have been proven to be very suitable for coupling with the high-molecular inert stabilization domain, since they largely retain their activity in the recombinant fusion protein of the invention. Besides, there are other suitable candidates, such as thrombin-like proteases and recombinant versions thereof isolated from snake venoms. In particular, recombinant forms or variants of the enzymes ancrod or batroxobin are suitable as fibrinogenase domain of the recombinant fusion protein.

The high molecular inert stabilization domain preferably relates to serum albumin, preferably animal or human serum albumin. In another variant, the inert stabilization domain of high molecular weight includes transferrin or variants of transferrin inactivated by genetic modifications. In another variant, the high-molecular inert stabilization domain comprises artificial amino acid sequences, such as PAS (Schlapschy et. al 2013) or XTEN (US 2013/0165389 A1). Further, antibodies or antibody fragments can be linked as a stabilization domain with the fibrinogenolytic enzyme. For prophylactic or therapeutic application in humans, monoclonal antibodies, humanized antibodies or antibody fragments thereof are preferably used as antibodies. Furthermore, variants of the aforementioned stabilization domains can also be used for the purpose according to the present invention. Other embodiments also provide for the use of synthetic domains or other inert protein domains, insofar as they are described in the prior art.

In a preferred embodiment the fusion protein comprises an amino acid sequence that comprises the enzyme ancrod and a stabilizing domain (e.g. serum albumin or IgG-Fc antibody fragment). Preferably, the fusion protein comprises an amino acid sequence or fibrinogenolytically effective fragments of this sequence, such as recited in SEQ ID NO. 2 or SEQ ID NO. 4. Fibrinogenolytically effective fragments of this sequence refer to sequence segments coding for the enzyme domain and the stabilizing domain and that are enzymatically active in the degradation of fibrinogen. In the concrete examples, e.g. a hexahistidine-tag (His-tag) was added to the fibrinogenolytic components for ease of purification and a signal peptide. Further, additional or alternative amino acids may be added to or removed from the sequences above.

The fusion proteins of the present invention are fibrinogenolytically highly effective and lead to a specific degradation of fibrinogen. As a secondary effect, a fibrinolytic effect can be detected when applied in organism, since the degradation products of the enzyme, desA-profibrin and desAA-fibrin monomers, form soluble fibrin complexes, which in turn lead to plasminogen activation through the stimulation of endogenous t-PA. This effect can be measured in vivi as an increase in plasmin concentration following application of the enzyme. This effect provides a further advantage, as high concentrations of plasminogen activator inhibitor (PAI-1) in case of injuries would lead to the failure of natural fibrin degradation and to adhesion.

By the C-terminal coupling of ancrod or another fibrinogenolytically active protein to a stabilization domain, for example to serum albumin or IgG-Fc antibody fragment, the residence time of the construct will be extended significantly in the peritoneal cavity compared to the native fibrinogenolytically active enzyme. The construct can, in this way, exhibit a much longer duration of action as it would be the case with a native ancrod molecule. By retaining the construct in the peritoneal cavity, the passage of the active substance in the bloodstream has been significantly reduced.

The present invention further relates to a pharmaceutical composition comprising a recombinant fusion protein as described above. The pharmaceutical composition comprises a pharmaceutically acceptable carrier, and can be applied as a solution directly into the affected wound area, such as the abdominal area. Thereby, the active substance prevents the formation of adhesions throughout the compartment, especially where injuries may have possibly occurred. Due to the high molecular weight, the recombinant fusion protein remains as active substance for a longer period of time in the peritoneal cavity and does not or only to a small extent enter into the blood circulation system. Thereby, systemic effects and side effects of natural substances (for example, of ancrod or batroxobin) are prevented or reduced. The active substance can be applied during or after the surgery in the peritoneal cavity once or more times. A single application is preferred so that further injections or infusions are not absolutely necessary. This advantage is due to the longer residence time of the recombinant construct into the abdominal area compared to the natural substances.

In a preferred embodiment, the recombinant fusion protein of the invention can be used in combination with other treatments or products. For example, a combination of the fusion protein with physical barrier methods of solid or liquid membranes, gels or sprays is conceivable. Preferably, these are biodegradable.

By the application of species-specific domains as a stabilizing domain (for example, human serum albumin (HSA) or a human IgG-Fc antibody fragment), the inventive recombinant fusion protein has a low immunogenicity and does not have an own pharmacodynamic effect. Due to the high molecular weight of preferably >50 kDa, a long biological durability is also guaranteed.

In order to develop an optimum prophylactic efficacy with the pharmaceutical composition of the invention, the fibrinogenolytic activity must be present throughout the entire period of wound healing. Preferably, the recombinant fusion protein is present at the site of action in an effective concentration. The time required for complete wound healing is between 1 - 8 days; for the prophylactic treatment, a period of 2 to 4 days is preferred. The enzymatic activity of the pharmaceutically effective solution, administered in the abdominal area, which is required for preventive or therapeutic efficacy, lies in the range between 0.01 and 10 units/ml over the entire period of wound healing. Preferably, concentrations of the fusion protein are used that are between 0.1 to 5 units/ml (units/ml). Preferably, the recombinant fusion protein will be used in an osmotically active medium (e.g. ico-dextrin solution).

The present invention further relates to a combined use of the fusion protein with other products, for the prevention of tissue adhesions (adhesions), particularly after surgery. For this purpose, membranes are used, which are made of oxidized regenerated cellulose, polytetrafluoroethylene, hyaluronic acid carboxy methyl cellulose or polyethylene glycol. Further, liquid adhesion barriers can be used, which separate the organs and tissues by hydroflotation. Preferably, hyaluronic acid, cross-linked hyaluronic acid or ico-dextrin is used.

The recombinant fusion protein of the invention is preferably embedded in a biocompatible, biodegradable matrix, which continuously releases the fusion protein during the initial healing phase, preferably, over a period of 2 to 4 days.

WAYS OF IMPLEMENTING THE INVENTION

The invention is illustrated in the following examples.

EXAMPLES

Example 1

Preparation of N-ancrod-Fc-fusion Protein

For the production of the composition of the invention a fusion protein was prepared, consisting of ancrod and the constant region of a human IgG1 antibody. Between the biologically active ancrod domain and the stabilizing domain formed by the IgG1-Fc antibody fragment, a glycine-alanine-linker is inserted. In order to improve secretion into the cell culture medium and to facilitate purification, the signal peptide of human serum albumin was added at the N-terminus. For the production, the sequence of ancrod protein (access number: ABN13428.1) was added at its C-terminus to the constant region of a human IgG1 (Uniprot acc.no. P01857-1, amino acids 104-330) via a flexible glycine-alanine linker. Subsequently, the HSA-signal peptide (amino acids 1 to 18), required for the purification was added. For the synthesis of cDNA coding for the fusion protein, the DNA codons were optimized for expression in human cells. At the 5' end of cDNA, restriction sites for NotI and XbaI were added, and at the 3' end, restriction sites for BstXI and HindiII, which allows the cloning of DNA into the appropriate vectors for a transient expression and/or for the production of stable cell lines. The resulting cDNA construct was produced synthetically.

This cDNA was cloned, amplified, and recloned into an expression vector for transient transfection. The correct insertion of cDNA was tested via a restriction digest. With the resulting plasmid, E. coli bacteria (DH5α) were then transformed and the strain was cultured in 0.8 litre of LB medium. From this, the plasmid DNA was isolated and the endotoxin solution was filtered sterile.

For transient expression of the protein, HEK-F cells were set up in serum-free suspension culture in a volume of 500 ml in shake flasks (approximately $2.5 \times 10^6$ cells/ml). Transfection of cells was carried out via a branched PEG-amino ester copolymer with a transfection mixture of about 10 μg DNA/$1 \times 10^7$ cells—DNA/coPEG33-1/6 (w/w). After the addition of valproic acid, the cell culture was cultivated for a further 7 days. Thereafter, the cell culture supernatant was harvested by centrifugation. Chromatography was performed in 50 mM MES buffer, pH 5.5.

The purification of the fusion protein was carried out by ion exchange chromatography. HiTrap SP FF Affinity Resin (GE Healthcare Europe GmbH, Freiburg, Germany) was used as column material. The elution of fusion protein was carried out by a sodium chloride gradient. Analysis of the eluate fractions was carried out by gel electrophoresis (SDS—PAGE) and suitable protein fractions were pooled and dialyzed, aliquoted and stored until further use at −20° C. against buffered saline (PBS).

The cDNA sequence of the construct is shown in SEQ ID NO 1:

Underlined are the inserted restriction sites. - The sequence encoding the fusion protein is shown in bold.

gcggccgccaccatgaaatgggtcacctttatctcccttctgttcctctt tagtagcgcctattctgtcatcggtggtgacgagtgcaatatcaacgagc atcgatttctggtggcagtgtatgaaggaaccaactggacctttatctgc ggcggggtccttattcacccagagtgggtcattaccgccgaacactgtgc tcggcgtcgaatgaatcttgtgttcgggatgcacaggaaatcagagaagt ttgatgacgaacaggaacggtatcccaagaagcggtacttcattcgatgc aacaaaacccggactagctgggatgaggacatcatgctgattcggctgaa caagcccgtgaataacagcgagcatattgctcctttgtcactgccttcca atccgcctattgtgggtagtgactgccgtgtgatgggctggggtagcatt aacagaaggatccacgtgcttagcgatgaacccagatgtgccaacatcaa tctccacaacttcaccatgtgtcatgggttgttccgcaagatgcctaaga agggacgcgtactctgtgctggcgatctgcgcgggtagacgggactcttgc -continued

```
aattcagatagtggaggacccctatctgcaacgaagagctgcatggcat tgtggccagaggcccaatccatgtgcacagcccaacaaaccagctctgt atactagcgtgtacgactacagggattgggtgaacaacgttatcgccggc aatgcaacctgtagtccaggcggcggcggagccggtggaggcggggcagg aggaggaggagctagagacaaaacacacacttgtccaccctgtcctgctc ccgaactgcttggtggaccagcgtgtttctgtttccgcctaagcccaaa gacaccctcatgatctcacggactcccgaagttacgtgtgtcgtagtaga cgtgtcacacgaagatcccgaggtcaagttcaactggtatgtggacggag ttgaggttcacaacgccaaaaccaaaccgagagaggagcagtacaactcc acatatagggtggtaagcgtgttgaccgtgctgcatcaggattggctgaa tggcaaagagtacaagtgcaaggtgtccaataaggctcttccagcaccca ttgagaaaacgatctccaaggcgaaaggccaacctcgtgaacctcaggtg tatactctccctccaagtcgcgatgagctcaccaagaaccaggtgtcttt gacatgcctcgtcaaagggttctacccatcagacatagccgtcgaatggg agtctaatggccaaccagagaataactacaagaccactcctccggttctg gatagtgatgggagcttctttctgtacagcaagctgacagtcgacaagtc ccgatggcagcagggtaatgtgttcagttgctctgtgatgcatgaagccc tgcataaccactatacccagaaaagcctgtctctgagcccaggaaagtaa tagaagctt
```

The resulting amino acid sequence is shown in SEQ ID NO 2:

```
MKWVTFISLL FLFSSAYSVI GGDECNINEH RFLVAVYEGT NWTFICGGVL       50

IHPEWVITAE HCARRRMNLV FGMHRKSEKF DDEQERYPKK RYFIRCNKTR      100

TSWDEDIMLI RLNKPVNNSE HIAPLSLPSN PPIVGSDCRV MGWGSINRRI      150

HVLSDEPRCA NINLHNFTMC HGLFRKMPKK GRVLCAGDLR GRRDSCNSDS      200

GGPLICNEEL HGIVARGPNP CAQPNKPALY TSVYDYRDWV NNVIAGNATC      250

SPGGGGAGGG GAGGGGARDK THTCPPCPAP ELLGGPSVFL FPPKPKDTLM      300

ISRTPEVTCV VVDVSHEDPE VKFNWYVDGV EVHNAKTKPR EEQYNSTYRV      350

VSVLTVLHQD WLNGKEYKCK VSNKALPAPI EKTISKAKGQ PREPQVYTLP      400

PSRDELTKNQ VSLTCLVKGF YPSDIAVEWE SNGQPENNYK TTPPVLDSDG      450

SFFLYSKLTV DKSRWQQGNV FSCSVMHEAL HNHYTQKSLS LSPGK           495
```

The amino acid sequence starts with the signal peptide of human serum albumin MKWVTFISLLFLFSSAYS shown (underlined), which is separated during secretion of the protein from the cell. The linker GGGGAGGGGAGGGGAR, arranged between the human serum albumin and the ancrod-domain, is connected to the C-terminus of ancrod (shown in bold).

Example 2

Preparation of N-ancrod-HSA-C Fusion Protein with His-Tag.

In this example, a further variant of an ancrod-based fusion protein is shown, consisting of ancrod, human serum albumin (HSA), a signal peptide of human serum albumin and a subsequent His-Tag. Between the biologically active domain and the stabilization domain formed by the human serum albumin, a glycine-/serin-linker is inserted. For the production, the sequence of ancrod protein (accession number: ABN13428.1) is merged C-terminally with the N-terminus of human serum albumin (HSA) (accession number: P02768, amino acids 25-609). Subsequently, the HSA signal peptide (amino acids 1 to 18) was added. The cDNA was processed as described above and the protein was expressed.

The cDNA sequence of the construct is shown in SEQ ID NO 3:

```
gcggccgctctagagccaccatgaaatgggttaccttcattagcctcctg ttcctgttttcctccgcctattctgttatcggtggtgacgagtgtaacat caacgagcataggttcctggtcgcagtgtatgagggcacaaactggacct tcatttgtggcggggtgctgattcacccagagtgggtaataacagcggag cattgtgcccgcagacgcatgaatctcgtgtttggaatgcatcgcaaaag cgagaaattcgatgatgaacaagaaaggtaccctaagaagcggtacttca ttcggtgcaacaagacaagaacttcatgggacgaggacatcatgctgatc cgtcttaacaagccggtaaataacagcgagcatatcgcaccactctcatt gcccagcaaccctcccatcgtgggaagcgattgcagagtgatggggtggg gctccatcaatagaaggattcacgtgctctctgatgaaccgcggtgtgcc aacattaatctgcataattttactatgtgccatggtctgtttcgcaaaat gcccaagaaaggaagagttctgtgtgcaggcgatctgagaggaaggagag actcttgcaactccgatagtggcgggccactgatatgcaacgaagagctt
```

-continued

```
cacggaatcgtggccagaggtcctaatccatgtgctcagcctaacaagcc cgctctgtacaccagcgtttatgactaccgggattgggtcaacaatgtca ttgccggaaatgccacctgttccctggcggcggcgggtcaggaggagga gggtctggtggcggcgggtctgacgcacataaaagcgaagtggctcaccg gtttaaagatctcggcgaagagaacttcaaagctcttgtattgattgcct tcgctcagtacttgcaacagtgccctttcgaggaccacgtgaaactggtg aatgaagtcacagaattcgctaagacgtgtgtggcggatgagagtgctga
```

```
gaactgtgacaagagtctgcacaccctgtttggggataaactgtgcactg tcgctactctgcgagaaacttatggcgaaatggccgactgctgcgccaag caggaacccgagagaaatgaatgctttctgcagcacaaagacgacaaccc taatctgccacgattggttcggcccgaggtggacgtaatgtgcacggctt tccacgacaatgaggaaaccttcctgaagaagtatctctacgaaatagct cgacggcatccctactttatgcacccgagctgctgttctttgcgaagcg ctataaggccgctttcacagaatgctgtcaagctgccgacaaggctgcct gtctcctcccaaaactggacgagctccgcgatgaggggaaggcaagcagt gccaaacagcgcctgaaatgcgcatcacttcagaaattcggagagcgcgc attcaaagcatgggcagtggctcgattgtcccagcgatttcctaaggctg aatttgccgaagtgtcaaagctggtgacagaccttaccaaagtccacaca gaatgctgccatggtgacttgctggagtgcgccgatgacagagccgatct ggccaagtacatctgtgaaaatcaggattccatctcctccaaactgaaag
```

-continued

```
aagcgtatgccatgtgcagaggattatctgagtgtcgtcctcaaccagct gtgcgtacttcacgaaaagacaccagtgtccgatagggtcactaaatgtt gcaccgaatctctggtgaatcggaggccctgtttctcagctctggaagtt gatgaaacctacgttccgaaggagttcaatgcagaaacgtttacctttca cgctgacatctgcacgctctctgagaaggagaggcagataaagaagcaaa cagccctggtagagctggttaaacacaagcccaaagcaacaaggagcag ctgaaagcggtgatggatgacttcgccgcgtttgtggagaagtgctgtaa ggccgacataaagaaacttgcttcgccgaagagggaaagaagcttgtgg cagctagccaagcagcccttgggttgcaccaccatcaccaccactaatag ccactgtgctggttcgaa
```

Underlined are the inserted restriction sites (5': NotI, XbaI; 3': BstXI, HindIII)—in bold, the sequence encoding the fusion protein sequence is shown in bold.

The resulting amino acid sequence is shown in SEQ ID No 4:

```
MKWVTFISLL FLFSSAYSVI GGDECNINEH RFLVAVYEGT NWTFICGGVL IHPEWVITAE   60
HCARRRMNLV FGMHRKSEKF DDEQERYPKK RYFIRCNKTR TSWDEDIMLI RLNKPVNNSE  120
HIAPLSLPSN PPIVGSDCRV MGWGSINRRI HVLSDEPRCA NINLHNFTMC HGLFRKMPKK  180
GRVLCAGDLR GRRDSCNSDS GGPLICNEEL HGIVARGPNP CAQPNKPALY TSVYDYRDWV  240
NNVIAGNATC SPGGGGSGGG GSGGGGSDAH KSEVAHRFKD LGEENFKALV LIAFAQYLQQ  300
CPFEDHVKLV NEVTEFAKTC VADESAENCD KSLHTLFGDK LCTVATLRET YGEMADCCAK  360
QEPERNECFL QHKDDNPNLP RLVRPEVDVM CTAFHDNEET FLKKYLYEIA RRHPYFYAPE  420
LLFFAKRYKA AFTECCQAAD KAACLLPKLD ELRDEGKASS AKQRLKCASL QKFGERAFKA  480
WAVARLSQRF PKAEFAEVSK LVTDLTKVHT ECCHGDLLEC ADDRADLAKY ICENQDSISS  540
KLKECCEKPL LEKSHCIAEV ENDEMPADLP SLAADFVESK DVCKNYAEAK DVFLGMFLYE  600
YARRHPDYSV VLLLRLAKTY ETTLEKCCAA ADPHECYAKV FDEFKPLVEE PQNLIKQNCE  660
LFEQLGEYKF QNALLVRYTK KVPQVSTPTL VEVSRNLGKV GSKCCKHPEA KRMPCAEDYL  720
SVVLNQLCVL HEKTPVSDRV TKCCTESLVN RRPCFSALEV DETYVPKEFN AETFTFHADI  780
CTLSEKERQI KKQTALVELV KHKPKATKEQ LKAVMDDFAA FVEKCCKADD KETCFAEEGK  840
KLVAASQAAL GLHHHHHH                                                858
```

-continued

```
aatgctgcgagaaacccctgctggagaagagccattgtattgctgaggtg gaaaacgatgagatgccagcggacctcccatcactggcagccgacttcgt cgagagtaaggacgtgtgtaagaactacgccgaagcgaaggatgtgtttc tcgggatgtttctgtacgaatatgcgcgtcgtcatcccgattatagcgtg gttctgctgcttaggcttgccaagacttacgaaaccaccctcgagaagtg ttgtgccgccgctgacccgcatgagtgctacgccaaagtatttgacgagt ttaagcctctggtcgaggagcctcagaacctgatcaaacagaactgcgag cttttcgagcagttgggtgaatacaaatttcagaatgccctgctcgtcag gtatactaagaaggtgccccaagtgtctacacctaccttggttgaggtca gccggaatctcggcaaggtcggcagcaaatgctgtaagcacccagaggca
```

Underlined are the inserted restriction sites (5': NotI, XbaI; 3': BstXI, HindIII)—in bold, the sequence encoding the fusion protein sequence is shown in bold.

The amino acid sequence starts with the signal peptide of human serum albumin MKWVTFISLLFLFSSAYS, which is separated during secretion of the protein from the cell. The linker GGGGSGGGGSGGGGS, arranged between the human serum albumin and the ancrod-domain, is connected to the N-terminus of serum albumin (shown in bold).

Example 3

Activity Test of the Produced Fusion Proteins for Their Fibrinogenolytic Enzyme Activity The activity test of the fusion protein was performed using fibrinogen as substrate (1 mg/ml) dissolved in 10 mM Tris-HCl, 0.15 M NaCl, pH 7.4. Each 500 µl of fibrinogen solution were pipetted into a cuvette. After 2 minutes, 100 µl sample or a positive control (batroxobin) was added. Thereafter, the increase in turbidity at 340 nm was determined by photometry over a period of one hour and the maximum slope of the curve was ascertained. The maximum slope of the curve is proportional to the enzymatic activity, which is converted into units/ml using a calibration curve.

Example 4

Treatment of Peritoneal Adhesions in Mammals

For preventive or therapeutic application in a mammal (e.g., a human or a laboratory animal), the recombinant fusion protein of the invention isolated and purified following expression, or a matching placebo was applied directly into the abdominal area of the test animal post surgery that triggered adhesions. To achieve an optimum effect, an enzymatic activity of between 0.01 and 10 U/ml is desired. The pharmaceutical solution comprises the fusion protein having an activity between 0.1 and 5 U/ml.

After administering the fusion protein, a fibrinolytic enzyme activity of the fusion protein that continues over several days can be detected while simultaneously maintaining the wound healing. Compared to placebo-treated animals, the amount and severity of adhesions occurring as part of the wound healing process will be drastically reduced.

Example 5

Pharmacological and Pharmacokinetic Properties of N-ancrod-HSA-C Fusion Proteins For the production of the fusion protein, the sequence of ancrod protein (accession number: ABN13428.1) was merged C-terminally with the N-terminus of human serum albumin (HSA) (accession number: P02768, amino acids 25-609). The enzymatic activity of the fusion protein is 24 U/ml.

Since native ancrod is unsuitable in a therapeutic application for the treatment of peritoneal adhesions, the resulting fusion protein was tested on its activity and disposition (residence time) in the abdominal area. FIG. 1 shows the enzyme activity in the fluid in the abdominal area after a single intra-peritoneal administration of native ancrod and ancrod fusion protein of the invention (AK03). It can be clearly seen that the native ancrod is unsuitable for therapeutic use because the intraperitoneally administered ancrod quickly leaves the abdominal area and thus only low concentrations are obtained, which additionally also fall within 6 hours to values close to the detection limit. In contrast, after administering a comparable dose of ancrod-fusion protein (AK03), significantly higher activity is achieved in the abdominal area, which still lies well within the therapeutically effective range, even after 6 hours.

Figure 2:
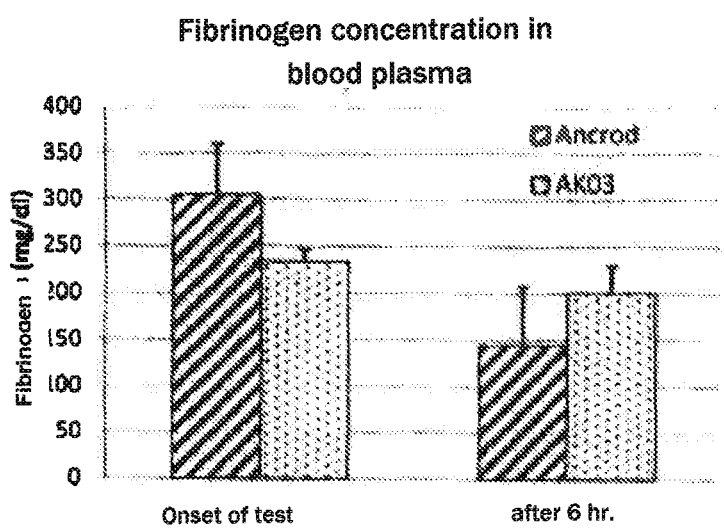
FIG. 2 shows the effect of ancrod and the ancrod-fusion protein of the invention (AK03) on fibrinogen concentration in blood plasma.

In FIG. 2, the effect of ancrod and the ancrod-fusion protein of the invention (AK03) on fibrinogen concentration in blood plasma is shown. The rapid passage of ancrod in the vascular system results here in a drop in the fibrinogen level in blood by more than 50%. AK03 migrates only very slowly into the bloodstream due to the changed molecular structure, and therefore results in a slight drop in fibrinogen level of 14%. Such small changes in fibrinogen concentrations fall within the physiological range and have no effect on blood clotting.

The ancrod fusion protein AK03 equipped with the stabilization domain thus shows a much more favourable pharmacokinetic behaviour than the native ancrod molecule.

These results show that the ancrod fusion protein exhibits similar enzymatic features as ancrod, but it is pharmacokinetically distinctly different. In particular, this leads to a longer residence time of the fusion protein in the peritoneal cavity and a lower passage of the substance into the bloodstream. Due to these properties, the fusion protein of the invention is particularly suitable for intraperitoneal application for the treatment / prevention of peritoneal adhesions.

Materials and Methods
Pharmacokinetics in Dogs

Three Beagle dogs were provided with venous and intraperitoneal indwelling catheters. A week after catheter implantation, animals received one single intraperitoneal injection of the test substance. 0.5 ml of samples of peritoneal fluid were taken at intervals of 0, 0.5; 1, 2, 4, 6, and 8 hours after administration of the substance; venous blood samples were taken for extracting citrated plasma at the time-points of 0, 0.5; 1, 2, 4, 6, 8, 16 and 24 hours. The fibrinogen concentration in the plasma samples was determined photometrically by the method according to Clauss. The enzyme activity in peritoneal fluid was determined by centrifugation of the samples using a kinetic turbidimetric method following addition of human fibrinogen.

Pharmacokinetics in Rats:

Sprague-Dawley rats received intraperitoneal injections of the test substance in a short inhalation anaesthesia. Simultaneously, a venous blood sample was taken. Thereafter, the animals were returned to the cage where they awoke after a short time. Six hours after administrating the substance, the animals were anesthetized again and the peritoneal fluid and a further blood sample were withdrawn for extracting citrate plasma. Both samples were immediately centrifuged after collection and snap frozen at −80° C. and analyzed at a later time with the methods described above.

BIBLIOGRAPHY

Arung, W.; Meurisse, M.; Detry, O. (2011): Pathophysiology and prevention of postoperative peritoneal adhesions. In: World J Gastroenterol 17 (41), pp 4545-4553.

Ashby, E. C; James, D. C; Ellis, H. (1970): The effect of intraperitoneal Malayan pit viper venom-on adhesion formation and peritoneal healing. In: Br J Surg 57 (1 1), S. 863 ad.

Binda, M; Hellebrekers, B W; Declerck, P J; Koninckx, P R (2009): Effect of Reteplase and PAI-1 antibodies on postoperative adhesion formation in a laparoscopic mouse model. In: Surgical Endoscopy 23 (5), pp 1018-1025.

Binnebosel, M.; Klink, C; Serno, J.; Jansen, P.; Trotha, K. of; Neumann, U.; Young, K. (2011): Chronological evaluation of inflammatory mediators during peritoneal adhesion formation using a rat model. In: Langenbeck's Archives of Surgery 396 (3), pp 371-378.

Broek, R. P. G. ten; Issa, Y.; van Santbrink, E J P; Bouvy, N. D.; Kruitwagen, R. F. P. M.; Jeekel, J. et al. (2013A): Burden of adhesions in abdominal and pelvic surgery: systematic review and met-analysis. In: BMJ 347, p f5588.

Broek, R P G ten; Kok-Krant, N.; Bakkum, E A; Bleichrodt, R P; van Goor, H. (2013B): Different surgical techniques to reduce post-operative adhesion formation: a systematic review and meta-analysis. In: Hum Reprod Update 19 (1), pp 12-25.

Brokelman, W J A; Lensvelt, M.; Borel Rinkes, I. H. M.; Klinkenbijl, J H G; Reijnen, M. M. P. J. (2011): Peritoneal changes due to laparoscopic surgery. In: Surg Endosc 25 (1), pp 1 -9.

Brummer, T. H. I.; Jalkanen, J.; Fraser, J.; Heikkinen, A-M.; Kauko, M.; Makinen, J. et al. (2011): FINHYST, a prospective study of 5279 hysterectomies: complications and their risk factors. In: Hum Reprod 26 (7) pp 1741-1751.

Buckman, R F Jr; Bordos, D.; Bell, W. R.; Cameron, J. L. (1975): Prevention of experimental postoperative adhesions by ancrod defibrinogenation. In: J Surg Res 18 (4), pp 377-384.

Chowdhury, S. M.; Hubbell, J. A. (1996): Adhesion prevention with ancrod released via a tissue-adherent hydrogel. In: J Surg Res 61 (1), pp 58-64.

Cohen, Z.; Senagore, A. J.; Dayton, M. T.; Koruda, M. J.; de Beck; Wolff, B. G. et al. (2005): Prevention of postoperative abdominal adhesions by a novel, glycerol/sodium hyaluronate/carboxymethylcellulose-based bioresorbable membrane: a prospective, randomized, evaluator-blinded multicenter study. In: Diseases of the colon and rectum 48 (6), pp 1130-1139.

Diamond, M. P.; Kruger, M.; Saed, G. M. (2004): Effect of Tisseel on expression of plasminogen activator and plasminogen activator tissue inhibitor-1. In: Fertility and sterility 81 (6), pp 1657-1664.

Ellis, H.; Moran, B. J.; Thompson, J. N.; Parker, M. C; Wilson, M. S.; Menzies, D. et al. (1999): Adhesion-related hospital readmissions after abdominal and pelvic surgery: a retrospective cohort study. In: Lancet 353 (9163), pp 1476-1480.

Fossum, G. T.; Silverberg, K. M.; Miller, C. E.; Diamond, M. P.; Holmdahl, L. (2011): Gynecologic use of Sepraspray Adhesion Barrier for reduction of adhesion development after laparoscopic myomectomy: a pilot study. In: Fertil Steril 96 (2), pp 487-491.

Hellebrekers, B. W. J.; Emeis, J. J.; Kooistra, T.; Trimbos, J. B.; Moore, N. R.; Zwinderman, K. H.; Trimbos-Kemper, T C (2005): A role for the fibrinolytic system in postsurgical adhesion formation. In: Fertil Steril 83 (1), pp 122-129.

Hellebrekers, B. W/; Trimbos-Kemper, T. C; Boesten, L; Jansen, F. W.; Kolkman, W.; Trimbos, J. B. et al. (2009): Preoperative predictors of postsurgical adhesion formation and the Prevention of Adhesions with Plasminogen Activator (PA-study): results of a clinical pilot study. In: Fertil Steril 91 (4), pp 1204-1214.

Hellebrekers, W. J.; Kooistra, T. (2011): Pathogenesis of postoperative adhesion formation. In: Br J Surg 98 (1 1), pp 1503-1516.

Hill-West, J. L.; Dunn, R. C.; Hubbell, J. A. (1995): Local release of fibrinolytic agents for adhesion prevention. In: J Surgical Research 59 (6), pp 759-763.

Klingler, P. J.; Floch, N. Ft.; Seelig, M. H.; Branton, S. A.; Wolfe, J. T.; Metzger, P. P. (1999): Seprafilm-induced peritoneal inflammation: a previously unknown complication. Report of a case. In: Diseases of the colon and rectum 42 (12), pp 1639-1643.

Kossi, J.; Salminen, P.; Rantala, A.; Laato, M. (2003): Population-based study of the surgical workload and economic impact of bowel obstruction caused by postoperative adhesions. In: Br J Surg 90 (11), pp 1441 -1444.

Parker, M. C; Wilson, M. S.; Menzies, D.; Sunderland, G.; Clark, D. N.; Knight, A. D.; Crowe, A. M. (2005): The SCAR-3 study: 5-year adhesion-related readmission risk Following lower abdominal surgical procedures. In: Colorectal Dis 7 (6), pp 551-558.

Parker, M. C; Ellis, H.; Moran, B. J.; Thompson, J. N.; Wilson, M. S.; Menzies, D. et al. (2001): Postoperative adhesions: ten-year follow-up of 12,584 patients undergoing lower abdominal surgery. In: Dis Colon Rectum 44 (6), pp 822-830.

Ray, N. F.; Denton, W. G.; Thamer, M.; Henderson, S. C; Perry, S. (1998): Abdominal adhesiolysis: inpatient care and expenditures in the United States in 1994. J Am Surg Coli 186 (1), pp 1 -9.

Saed, G. M.; Diamond, M. P. (2004): Molecular characterization of postoperative adhesions: the adhesion phenotype. In: The Journal of the American Association of Gynecologic Laparoscopists 11 (3), pp 307-314.

SCAR Group (2013): Pathogenesis, consequences, and control of peritoneal adhesions in gynaecologic surgery: a committee opinion. Fertil Steril 99 (6), pp 1550-1555.

Schnüriger, B.; Barmparas, G.; Branco, B. C; Lustenberger, T.; Inaba, K.; Demetriades, D. (2011): Prevention of postoperative peritoneal adhesions: a review of the literature. The American Journal of Surgery 201 (1), pp 111-121.

Schlapschy M, Binder U, Börger C, et al. (2013) PASylation: a biological alternative to PEGylation for extending the plasma half-life of pharmaceutically active proteins. Protein Eng Des Sel. 26 (8): 489-501.

Sikirica, V.; Bapat, B.; Candrilli, S. D.; Davis, K. L; Wilson, M.; Johns, A. (2011): The inpatient burden of abdominal and gynaecological adhesiolysis in the US. BMC Surg 11, p. 13.

Wallwiener, M.; Koninckx, P. R.; Hackethal, A.; Brömann, H.; Lundorff, P.; Mara, M. et al. (2014): A European survey on awareness of post-surgical adhesions among gynaecological surgeons. In: Surg Gynecol 11 (2), pp 105-112.

The invention claimed is:

1. A pharmaceutical composition comprising a recombinant fusion protein comprising ancrod, or a recombinant variant of ancrod having fibrinogenolytic activity, wherein the ancrod or variant ancrod is connected by a linker at the C-terminal amino acid to the N-terminus of an amino acid sequence of at least one high-molecular weight inert stabilization domain with a molecular weight of >50 kDa that provides non-specific bonding to a mesothelium surface lining a peritoneal cavity of a patient and reduces transport of the fusion protein through a peritoneal membrane, the inert stabilization domain comprising a dimer or multimer of an IgG-Fc antibody fragment; and a pharmaceutically acceptable carrier that comprises a biodegradable matrix that provides for continuous intraperitoneal release of the recombinant fusion protein.

2. The pharmaceutical composition according to claim 1, wherein the inert stabilization domain comprises a dimer of the IgG-Fc antibody fragment.

3. The pharmaceutical composition according to claim 1, wherein the pharmaceutically acceptable carrier comprises an osmotically active medium.

4. The pharmaceutical composition according to claim 1, wherein the recombinant fusion protein comprises in order from amino-terminus to carboxy-terminus, ancrod or a recombinant variant of ancrod having fibrinogenolytic activity; a glycine-serine linker having the sequence (GGGGGS) x, where G=glycine; S=serine; x=number of repetitions >1; and the IgG-FC antibody fragment.

5. The pharmaceutical composition according to claim 1, in which the pharmaceutical carrier further comprises hyaluronic acid, cross-linked hyaluronic acid or ico-dextrin.

6. A method for preparing a pharmaceutical composition, comprising combining a recombinant fusion protein comprising ancrod, or a recombinant variant of ancrod having fibrinogenolytic activity, wherein the ancrod or variant ancrod is connected by a linker at the C-terminal amino acid to the N-terminus of an amino acid sequence of at least one high-molecular weight inert stabilization domain with a molecular weight of >50 kDa that provides non-specific bonding to a mesothelium surface lining a peritoneal cavity of a patient and reduces transport of the fusion protein through a peritoneal membrane, the inert stabilization domain comprising a dimer or a multimer of an IgG-Fc antibody fragment, and a pharmaceutically acceptable carrier comprising a biodegradable matrix for continuous intraperitoneal release of the recombinant fusion protein.

7. The method according to claim 6, wherein the inert stabilization domain comprises a dimer of the IgG-Fc antibody fragment.

8. The method according to claim 6, wherein the recombinant fusion protein comprises the amino acid sequence set forth in SEQ ID NO: 2.

* * * * *

SEQUENCE LISTING

<160> NUMBER OF SEQ ID NOS: 4

<210> SEQ ID NO 1
<211> LENGTH: 1509
<212> TYPE: DNA
<213> ORGANISM: Artificial
<220> FEATURE:
<223> OTHER INFORMATION: Fusion between Ancrod and the human Fc IgG1 antibody

<400> SEQUENCE: 1

```
gcggccgcca ccatgaaatg ggtcaccttt atctccttc tgttcctctt tagtagcgcc      60
tattctgtca tcggtggtga cgagtgcaat atcaacgagc atcgatttct ggtgcagtg     120 tatgaaggaa ccaactggac ctttatctgc ggcgggtcc ttattcaccc agagtgggtc     180
```

```
attaccgccg aacactgtgc tcggcgtcga atgaatcttg tgttcgggat gcacaggaaa    240
tcagagaagt ttgatgacga acaggaacgg tatcccaaga agcggtactt cattcgatgc    300
aacaaaaccc ggactagctg ggatgaggac atcatgctga ttcggctgaa caagcccgtg    360
aataacagcg agcatattgc tcctttgtca ctgccttcca atccgcctat tgtgggtagt    420
gactgccgtg tgatgggctg gggtagcatt aacagaagga tccacgtgct tagcgatgaa    480
cccagatgtg ccaacatcaa tctccacaac ttcaccatgt gtcatgggtt gttccgcaag    540
atgcctaaga agggacgcgt actctgtgct ggcgatctgc gcggtagacg ggactcttgc    600
aattcagata gtggaggacc ccttatctgc aacaagagc tgcatggcat gtgtggccaga    660
ggccccaatc catgtgcaca gcccaacaaa ccagctctgt atactagcgt gtacgactac    720
agggattggg tgaacaacgt tatcgccggc aatgcaacct gtagtccagg cggcggcgga    780
gccggtggag gcggggcagg aggaggagga gctagagaca aaacacacac ttgtccaccc    840
tgtcctgctc ccgaactgct tggtggaccc agcgtgtttc tgtttccgcc taagcccaaa    900
gacaccctca tgatctcacg gactcccgaa gttacgtgtg tcgtagtaga cgtgtcacac    960
gaagatcccg aggtcaagtt caactggtat gtggacggag ttgaggttca acgcgccaaa   1020
accaaaccga gagaggagca gtacaactcc acatataggg tggtaagcgt gttgaccgtg   1080
ctgcatcagg attggctgaa tggcaaagag tacaagtgca aggtgtccaa taaggctctt   1140
ccagcaccca ttgagaaaac gatctccaag gcgaaaggcc aacctcgtga acctcaggtg   1200
tatactctcc ctccaagtcg cgatgagctc accaagaacc aggtgtcttt gacatgcctc   1260
gtcaaagggt tctacccatc agacatagcc gtcgaatggg agtctaatgg ccaaccagag   1320
aataactaca agaccactcc tccggttctg gatagtgatg ggagcttctt tctgtacagc   1380
aagctgacag tcgacaagtc ccgatggcag cagggtaatg tgttcagttg ctctgtgatg   1440
catgaagccc tgcataacca ctatacccag aaaagcctgt ctctgagccc aggaaagtaa   1500
tagaagctt                                                           1509
```

<210> SEQ ID NO 2
<211> LENGTH: 495
<212> TYPE: PRT
<213> ORGANISM: Artificial
<220> FEATURE:
<223> OTHER INFORMATION: Fusion between Ancrod and the human Fc IgG1
      antibody

<400> SEQUENCE: 2

Met Lys Trp Val Thr Phe Ile Ser Leu Leu Phe Leu Phe Ser Ser Ala
1               5                   10                  15

Tyr Ser Val Ile Gly Gly Asp Glu Cys Asn Ile Asn Glu His Arg Phe
            20                  25                  30

Leu Val Ala Val Tyr Glu Gly Thr Asn Trp Thr Phe Ile Cys Gly Gly
        35                  40                  45

Val Leu Ile His Pro Glu Trp Val Ile Thr Ala Glu His Cys Ala Arg
    50                  55                  60

Arg Arg Met Asn Leu Val Phe Gly Met His Arg Lys Ser Glu Lys Phe
65                  70                  75                  80

Asp Asp Glu Gln Glu Arg Tyr Pro Lys Lys Arg Tyr Phe Ile Arg Cys
                85                  90                  95

Asn Lys Thr Arg Thr Ser Trp Asp Glu Asp Ile Met Leu Ile Arg Leu
            100                 105                 110

Asn Lys Pro Val Asn Asn Ser Glu His Ile Ala Pro Leu Ser Leu Pro

```
            115                 120                 125
Ser Asn Pro Ile Val Gly Ser Asp Cys Arg Val Met Gly Trp Gly
    130                 135                 140
Ser Ile Asn Arg Arg Ile His Val Leu Ser Asp Glu Pro Arg Cys Ala
145                 150                 155                 160
Asn Ile Asn Leu His Asn Phe Thr Met Cys His Gly Leu Phe Arg Lys
                165                 170                 175
Met Pro Lys Lys Gly Arg Val Leu Cys Ala Gly Asp Leu Arg Gly Arg
            180                 185                 190
Arg Asp Ser Cys Asn Ser Asp Ser Gly Gly Pro Leu Ile Cys Asn Glu
        195                 200                 205
Glu Leu His Gly Ile Val Ala Arg Gly Pro Asn Pro Cys Ala Gln Pro
    210                 215                 220
Asn Lys Pro Ala Leu Tyr Thr Ser Val Tyr Asp Tyr Arg Asp Trp Val
225                 230                 235                 240
Asn Asn Val Ile Ala Gly Asn Ala Thr Cys Ser Pro Gly Gly Gly
                245                 250                 255
Ala Gly Gly Gly Gly Ala Gly Gly Gly Ala Arg Asp Lys Thr His
            260                 265                 270
Thr Cys Pro Pro Cys Pro Ala Pro Glu Leu Leu Gly Gly Pro Ser Val
        275                 280                 285
Phe Leu Phe Pro Pro Lys Pro Lys Asp Thr Leu Met Ile Ser Arg Thr
    290                 295                 300
Pro Glu Val Thr Cys Val Val Val Asp Val Ser His Glu Asp Pro Glu
305                 310                 315                 320
Val Lys Phe Asn Trp Tyr Val Asp Gly Val Glu Val His Asn Ala Lys
                325                 330                 335
Thr Lys Pro Arg Glu Glu Gln Tyr Asn Ser Thr Tyr Arg Val Val Ser
            340                 345                 350
Val Leu Thr Val Leu His Gln Asp Trp Leu Asn Gly Lys Glu Tyr Lys
        355                 360                 365
Cys Lys Val Ser Asn Lys Ala Leu Pro Ala Pro Ile Glu Lys Thr Ile
    370                 375                 380
Ser Lys Ala Lys Gly Gln Pro Arg Glu Pro Gln Val Tyr Thr Leu Pro
385                 390                 395                 400
Pro Ser Arg Asp Glu Leu Thr Lys Asn Gln Val Ser Leu Thr Cys Leu
                405                 410                 415
Val Lys Gly Phe Tyr Pro Ser Asp Ile Ala Val Glu Trp Glu Ser Asn
            420                 425                 430
Gly Gln Pro Glu Asn Asn Tyr Lys Thr Thr Pro Pro Val Leu Asp Ser
        435                 440                 445
Asp Gly Ser Phe Phe Leu Tyr Ser Lys Leu Thr Val Asp Lys Ser Arg
    450                 455                 460
Trp Gln Gln Gly Asn Val Phe Ser Cys Ser Val Met His Glu Ala Leu
465                 470                 475                 480
His Asn His Tyr Thr Gln Lys Ser Leu Ser Leu Ser Pro Gly Lys
                485                 490                 495

<210> SEQ ID NO 3
<211> LENGTH: 2618
<212> TYPE: DNA
<213> ORGANISM: Artificial
<220> FEATURE:
<223> OTHER INFORMATION: Fusion between Ancrod and human serum albumin
```

<400> SEQUENCE: 3

```
gcggccgctc tagagccacc atgaaatggg ttaccttcat tagcctcctg ttcctgtttt      60
cctccgccta ttctgttatc ggtggtgacg agtgtaacat caacgagcat aggttcctgg     120
tcgcagtgta tgagggcaca aactggacct tcatttgtgg cggggtgctg attcacccag     180
agtgggtaat aacagcggag cattgtgccc gcagacgcat gaatctcgtg tttggaatgc     240
atcgcaaaag cgagaaattc gatgatgaac aagaaaggta ccctaagaag cggtacttca     300
ttcggtgcaa caagacaaga acttcatggg acgaggacat catgctgatc cgtcttaaca     360
agccggtaaa taacagcgag catatcgcac cactctcatt gcccagcaac cctcccatcg     420
tgggaagcga ttgcagagtg atggggtggg gctccatcaa tagaaggatt cacgtgctct     480
ctgatgaacc gcggtgtgcc aacattaatc tgcataattt tactatgtgc catggtctgt     540
ttcgcaaaat gcccaagaaa ggaagagttc tgtgtgcagg cgatctgaga ggaaggagag     600
actcttgcaa ctccgatagt ggcgggccac tgatatgcaa cgaagagctt cacggaatcg     660
tggccagagg tcctaatcca tgtgctcagc ctaacaagcc cgctctgtac accagcgttt     720
atgactaccg ggattgggtc aacaatgtca ttgccggaaa tgccacctgt tccctggcg      780
gcggcgggtc aggaggagga gggtctggtg gcggcgggtc tgacgcacat aaaagcgaag     840
tggctcaccg gtttaaagat ctcggcgaag agaacttcaa agctcttgta ttgattgcct     900
tcgctcagta cttgcaacag tgcccttccg aggaccacgt gaaactggtg aatgaagtca     960
cagaattcgc taagacgtgt gtggcggatg agagtgctga gaactgtgac aagagtctgc    1020
acaccctgtt tggggataaa ctgtgcactg tcgctactct gcgagaaact tatggcgaaa    1080
tggccgactg ctgcgccaag caggaacccg agagaaatga atgctttctg cagcacaaag    1140
acgcaaaccc taatctgcca cgattggttc ggccccgaggt ggacgtaatg tgcacggctt    1200
tccacgacaa tgaggaaacc ttcctgaaga agtatctcta cgaaatagct cgacggcatc    1260
cctactttta tgcacccgag ctgctgttct ttgcgaagcg ctataaggcc gctttcacag    1320
aatgctgtca agctgccgac aaggctgcct gtctcctccc aaaactggac gagctccgcg    1380
atgaggggaa ggcaagcagt gccaaacagc gcctgaaatg cgcatcactt cagaaattcg    1440
gagagcgcgc attcaaagca tgggcagtgg ctcgattgtc ccagcgattt cctaaggctg    1500
aatttgccga agtgtcaaag ctggtgacag accttaccaa agtccacaca gaatgctgcc    1560
atggtgactt gctggagtgc gccgatgaca gagccgatct ggccaagtac atctgtgaaa    1620
atcaggattc catctcctcc aaactgaaag aatgctgcga aaaccccctg ctggagaaga    1680
gccattgtat tgctgaggtg gaaaacgatg agatgccagc ggacctccca tcactggcag    1740
ccgacttcgt cgagagtaag gacgtgtgta agaactacgc cgaagcgaag gatgtgtttc    1800
tcgggatgtt tctgtacgaa tatgcgcgtc gtcatcccga ttatagcgtg gttctgctgc    1860
ttaggcttgc caagacttac gaaaccacct cgagaagtg ttgtgccgcc gctgacccgc     1920
atgagtgcta cgccaaagta tttgacgagt ttaagcctct ggtcgaggag cctcagaacc    1980
tgatcaaaca gaactgcgag cttttcgagc agttgggtga atacaaattt cagaatgccc    2040
tgctcgtcag gtatactaag aaggtgcccc aagtgtctac acctaccttg gttgaggtca    2100
gccggaatct cggcaaggtc ggcagcaaat gctgtaagca cccagaggca aagcgtatgc    2160
catgtgcaga ggattatctg agtgtcgtcc tcaaccagct gtgcgtactt cacgaaaaga    2220
caccagtgtc cgatagggtc actaaatgtt gcaccgaatc tctggtgaat cggaggccct    2280
gtttctcagc tctggaagtt gatgaaacct acgttccgaa ggagttcaat gcagaaacgt    2340
```

```
ttacctttca cgctgacatc tgcacgctct ctgagaagga gaggcagata aagaagcaaa    2400
cagccctggt agagctggtt aaacacaagc ccaaagcaac aaaggagcag ctgaaagcgg    2460
tgatggatga cttcgccgcg tttgtggaga agtgctgtaa ggccgacgat aaagaaactt    2520
gcttcgccga gagggaaag aagcttgtgg cagctagcca agcagccctt gggttgcacc    2580
accatcacca ccactaatag ccactgtgct ggttcgaa                           2618
```

<210> SEQ ID NO 4
<211> LENGTH: 858
<212> TYPE: PRT
<213> ORGANISM: Artificial
<220> FEATURE:
<223> OTHER INFORMATION: Fusion between Ancrod and human serum albumin

<400> SEQUENCE: 4

```
Met Lys Trp Val Thr Phe Ile Ser Leu Leu Phe Leu Phe Ser Ser Ala
1               5                   10                  15

Tyr Ser Val Ile Gly Gly Asp Glu Cys Asn Ile Asn Glu His Arg Phe
            20                  25                  30

Leu Val Ala Val Tyr Glu Gly Thr Asn Trp Thr Phe Ile Cys Gly Gly
        35                  40                  45

Val Leu Ile His Pro Glu Trp Val Ile Thr Ala Glu His Cys Ala Arg
    50                  55                  60

Arg Arg Met Asn Leu Val Phe Gly Met His Arg Lys Ser Glu Lys Phe
65                  70                  75                  80

Asp Asp Glu Gln Glu Arg Tyr Pro Lys Lys Arg Tyr Phe Ile Arg Cys
                85                  90                  95

Asn Lys Thr Arg Thr Ser Trp Asp Glu Asp Ile Met Leu Ile Arg Leu
            100                 105                 110

Asn Lys Pro Val Asn Asn Ser Glu His Ile Ala Pro Leu Ser Leu Pro
        115                 120                 125

Ser Asn Pro Pro Ile Val Gly Ser Asp Cys Arg Val Met Gly Trp Gly
    130                 135                 140

Ser Ile Asn Arg Arg Ile His Val Leu Ser Asp Glu Pro Arg Cys Ala
145                 150                 155                 160

Asn Ile Asn Leu His Asn Phe Thr Met Cys His Gly Leu Phe Arg Lys
                165                 170                 175

Met Pro Lys Lys Gly Arg Val Leu Cys Ala Gly Asp Leu Arg Gly Arg
            180                 185                 190

Arg Asp Ser Cys Asn Ser Asp Ser Gly Gly Pro Leu Ile Cys Asn Glu
        195                 200                 205

Glu Leu His Gly Ile Val Ala Arg Gly Pro Asn Pro Cys Ala Gln Pro
    210                 215                 220

Asn Lys Pro Ala Leu Tyr Thr Ser Val Tyr Asp Tyr Arg Asp Trp Val
225                 230                 235                 240

Asn Asn Val Ile Ala Gly Asn Ala Thr Cys Ser Pro Gly Gly Gly Gly
                245                 250                 255

Ser Gly Gly Gly Gly Ser Gly Gly Gly Ser Asp Ala His Lys Ser
            260                 265                 270

Glu Val Ala His Arg Phe Lys Asp Leu Gly Glu Glu Asn Phe Lys Ala
        275                 280                 285

Leu Val Leu Ile Ala Phe Ala Gln Tyr Leu Gln Gln Cys Pro Phe Glu
    290                 295                 300

Asp His Val Lys Leu Val Asn Glu Val Thr Glu Phe Ala Lys Thr Cys
```

```
            305                 310                 315                 320
Val Ala Asp Glu Ser Ala Glu Asn Cys Asp Lys Ser Leu His Thr Leu
                325                 330                 335

Phe Gly Asp Lys Leu Cys Thr Val Ala Thr Leu Arg Glu Thr Tyr Gly
                340                 345                 350

Glu Met Ala Asp Cys Cys Ala Lys Gln Glu Pro Glu Arg Asn Glu Cys
                355                 360                 365

Phe Leu Gln His Lys Asp Asp Asn Pro Asn Leu Pro Arg Leu Val Arg
                370                 375                 380

Pro Glu Val Asp Val Met Cys Thr Ala Phe His Asp Asn Glu Glu Thr
385                 390                 395                 400

Phe Leu Lys Lys Tyr Leu Tyr Glu Ile Ala Arg Arg His Pro Tyr Phe
                405                 410                 415

Tyr Ala Pro Glu Leu Leu Phe Phe Ala Lys Arg Tyr Lys Ala Ala Phe
                420                 425                 430

Thr Glu Cys Cys Gln Ala Ala Asp Lys Ala Ala Cys Leu Leu Pro Lys
                435                 440                 445

Leu Asp Glu Leu Arg Asp Glu Gly Lys Ala Ser Ser Ala Lys Gln Arg
                450                 455                 460

Leu Lys Cys Ala Ser Leu Gln Lys Phe Gly Glu Arg Ala Phe Lys Ala
465                 470                 475                 480

Trp Ala Val Ala Arg Leu Ser Gln Arg Phe Pro Lys Ala Glu Phe Ala
                485                 490                 495

Glu Val Ser Lys Leu Val Thr Asp Leu Thr Lys Val His Thr Glu Cys
                500                 505                 510

Cys His Gly Asp Leu Leu Glu Cys Ala Asp Asp Arg Ala Asp Leu Ala
                515                 520                 525

Lys Tyr Ile Cys Glu Asn Gln Asp Ser Ile Ser Ser Lys Leu Lys Glu
                530                 535                 540

Cys Cys Glu Lys Pro Leu Leu Glu Lys Ser His Cys Ile Ala Glu Val
545                 550                 555                 560

Glu Asn Asp Glu Met Pro Ala Asp Leu Pro Ser Leu Ala Ala Asp Phe
                565                 570                 575

Val Glu Ser Lys Asp Val Cys Lys Asn Tyr Ala Glu Ala Lys Asp Val
                580                 585                 590

Phe Leu Gly Met Phe Leu Tyr Glu Tyr Ala Arg Arg His Pro Asp Tyr
                595                 600                 605

Ser Val Val Leu Leu Leu Arg Leu Ala Lys Thr Tyr Glu Thr Thr Leu
                610                 615                 620

Glu Lys Cys Cys Ala Ala Ala Asp Pro His Glu Cys Tyr Ala Lys Val
625                 630                 635                 640

Phe Asp Glu Phe Lys Pro Leu Val Glu Glu Pro Gln Asn Leu Ile Lys
                645                 650                 655

Gln Asn Cys Glu Leu Phe Glu Gln Leu Gly Glu Tyr Lys Phe Gln Asn
                660                 665                 670

Ala Leu Leu Val Arg Tyr Thr Lys Lys Val Pro Gln Val Ser Thr Pro
                675                 680                 685

Thr Leu Val Glu Val Ser Arg Asn Leu Gly Lys Val Gly Ser Lys Cys
                690                 695                 700

Cys Lys His Pro Glu Ala Lys Arg Met Pro Cys Ala Glu Asp Tyr Leu
705                 710                 715                 720

Ser Val Val Leu Asn Gln Leu Cys Val Leu His Glu Lys Thr Pro Val
                725                 730                 735
```

-continued

```
Ser Asp Arg Val Thr Lys Cys Cys Thr Glu Ser Leu Val Asn Arg Arg
            740             745             750

Pro Cys Phe Ser Ala Leu Glu Val Asp Glu Thr Tyr Val Pro Lys Glu
        755             760             765

Phe Asn Ala Glu Thr Phe Thr Phe His Ala Asp Ile Cys Thr Leu Ser
    770             775             780

Glu Lys Glu Arg Gln Ile Lys Lys Gln Thr Ala Leu Val Glu Leu Val
785             790             795             800

Lys His Lys Pro Lys Ala Thr Lys Glu Gln Leu Lys Ala Val Met Asp
            805             810             815

Asp Phe Ala Ala Phe Val Glu Lys Cys Cys Lys Ala Asp Asp Lys Glu
            820             825             830

Thr Cys Phe Ala Glu Glu Gly Lys Lys Leu Val Ala Ala Ser Gln Ala
        835             840             845

Ala Leu Gly Leu His His His His His His
    850             855
```